United States Patent [19]

Fuchs et al.

[11] Patent Number: 4,772,629
[45] Date of Patent: Sep. 20, 1988

[54] OPTICALLY ACTIVE ISOMERS OF TRANS-3-(2-CHLORO-2-(4-CHLORO-PHENYL)-VINYL)-2,2-DIMETHYL-CYCLO-PROPANE-1-CARBOXYLIC ACID ALPHA-CYANO-4-FLUORO-3-PHENOXY-BENZYL ESTER AND THEIR USE AS ECTOPARASITICIDES

[75] Inventors: Rainer Fuchs; Wilhelm Stendel, both of Wuppertal, Fed. Rep. of Germany

[73] Assignee: Bayer Aktiengesellschaft, Leverkusen, Fed. Rep. of Germany

[21] Appl. No.: 840,355

[22] Filed: Mar. 17, 1986

Related U.S. Application Data

[63] Continuation of Ser. No. 595,029, Mar. 30, 1984, abandoned, which is a continuation of Ser. No. 414,133, Sep. 2, 1982, abandoned, which is a continuation of Ser. No. 293,791, Aug. 18, 1981, abandoned.

[30] Foreign Application Priority Data

Sep. 3, 1980 [DE] Fed. Rep. of Germany ....... 3033158

[51] Int. Cl.$^4$ .................... C07C 121/75; A01N 53/00
[52] U.S. Cl. .................................... 514/521; 558/398
[58] Field of Search ............... 558/398; 514/521, 321; 581/391

[56] References Cited
U.S. PATENT DOCUMENTS 4,276,306 6/1981 Fuchs et al. ........................ 514/521

Primary Examiner—Anton H. Sutto
Attorney, Agent, or Firm—Sprung Horn Kramer & Woods

[57] ABSTRACT

The invention relates to optically active isomers of trans-3-(2-chloro-2-(4-chloro-phenyl)-vinyl-2,2-dimethyl-cyclopropane-1-carboxylic acid α-cyano-4-fluoro-3-phenoxy-benzyl ester of Formula (I), to methods for the preparation of said optically active isomers, to compositions containing said optically active isomers and to the use of said optically active isomers and compositions for their ectoparasiticidal activity.

5 Claims, No Drawings

OPTICALLY ACTIVE ISOMERS OF TRANS-3-(2-CHLORO-2-(4-CHLORO-PHENYL)-VINYL)-2,2-DIMETHYL-CYCLOPROPANE-1-CARBOXYLIC ACID ALPHA-CYANO-4-FLUORO-3-PHENOXY-BENZYL ESTER AND THEIR USE AS ECTOPARASITICIDES

This application is a continuation of Ser. No. 595,029, filed Mar. 30, 1984; which is a continuation of Ser. No. 414,133, filed Sept. 2, 1982; which is a continuation of Ser. No. 293,791, filed Aug. 18, 1981, all now abandoned.

The invention relates to certain new optically active isomers of trans-3-(2-chloro-2-(4-chloro-phenyl)vinyl)-2,2-dimethyl-cyclopropane-1-carboxylic acid α-cyano-4-fluoro-3-phenoxy-benzyl ester, to processes for their production and to their use as ectoparasiticides.

It has already been disclosed that mixtures of the (±)-cis and (±)-trans forms of 3-(E/Z-2-chloro-2-(4-chloro-phenyl)-vinyl)-2,2-dimethyl-cyclopropane-1-carboxylic acid (±)-(α-cyano-4-fluoro-3-phenoxy-benzyl)ester have an insecticidal and acaricidal action (see DE-OS (German Published Specification) No. 2,730,515, Example 17).

Furthermore, German Patent Application No. P 2,936,864 relates to racemic isomer mixtures of trans-3-)2-chloro-2-(4-chloro-phenyl)-vinyl)-2,2-dimethyl-cyclopropane-1-carboxylic acid α-cyano-4-fluoro-3-phenoxy-benzyl ester.

The present invention now provides, as new compounds, optically active isomers of trans-3-(2-chloro-2-(4-chlorophenyl)-vinyl)-2,2-dimethyl-cyclopropane-1-carboxylic acid α-cyano-4-fluoro-3-phenoxy-benzyl ester of the formula

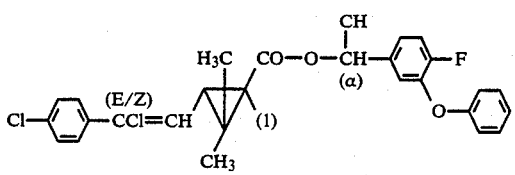

in which (a) the configuration at the cyclopropane-C atom (1) is R or S, that is to say the acids on which the compounds of the formula (I) are based rotate the plane of linearly polarised light to the right (+) or to the left (−) (this variable being indicated by the symbol "[1]");

(b) the configuration at the C—C double bond is E and/or Z (this variable being indicated by the symbol "[2]") and;

(c) the configuration at the α-C atom is R and/or S (this variable being indicated by the symbol "[3]"), the isomers being characterised by the following combinations of variables:

| Isomer No. | [1](*)() | [2]() | [3](**) |
| --- | --- | --- | --- |
| 1. | (+) | E/Z | R/S |
| 2. | (+) | E | R/S |
| 3. | (+) | Z | R/S |
| 4. | (+) | E/Z | S |
| 5. | (+) | E | S |
| 6. | (+) | Z | S |
| 7. | (−) | E/Z | R/S |
| 8. | (−) | E | R/S |
| 9. | (−) | Z | R/S |
| 10. | (−) | E/Z | S |
| 11. | (−) | E | S |
| 12. | (−) | Z | S |

(*)The symbols (+) and (−) relate to the direction in which linearly polarised light is rotated by the acids on which the compounds of the formula (I) are based; the corresponding absolute configurations (R and S) at the cyclopropane ring are not known, but the optically active acids are characterised unambiguously by stating the rotation of the linearly polarised light.

(**)The symbols (+) and (−), "E" and "Z" or "R" and "S" represent compounds of the formula (I) which are enriched to the extent of more than 60% by weight, preferably to the extent of more than 90% by weight, with the iomers of the particular configuration given; "E/Z" and "R/S" represent compounds of the formula (I) in which the isomers are present approximately in the ratio 1:1, that is to say in a ratio between 60:40 and 40:60.

Preferred isomers of the present invention are the abovementioned isomers 1 to 6; isomers 1, 3, 4 and 6 being particularly preferred.

The new compounds of the present invention are distinguished by a high ectoparasiticidal activity.

According to the present invention there is further provided a process for the preparation of a compound of the present invention, characterised in that a corresponding optically active isomer of trans-3-(2-chloro-2-(4-chloro-phenyl)-vinyl)-2,2-dimethyl-cyclopropane-1-carboxylic acid chloride of the formula

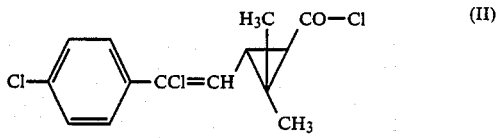

is reacted with, if appropriate, a corresponding optical isomer of α-cyano-4-fluoro-3-phenoxy-benzyl alcohol of the formula

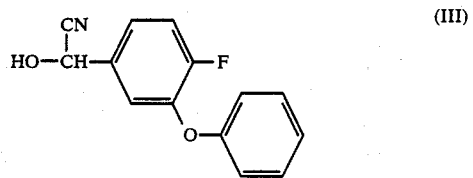

if appropriate in the presence of an acid acceptor and/or in the presence of a diluent, or, in the case where the configuration at the α-C atom is to be "R/S" (as hereinbefore defined), is reacted with 4-fluoro-3-phenoxy-benzaldehyde of the formula

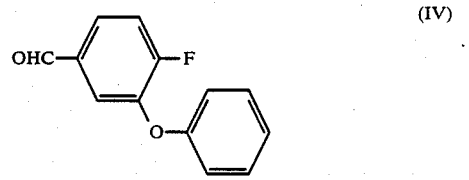

in the presence of at least the equimolar amount of an alkali metal cyanide, if appropriate in the presence of a catayst and if appropriate using a diluent.

Surprisingly, the new compounds of the present invention, in particular the isomers 1, 3, 4 and 6 exhibit a considerably more powerful insecticidal and acaricidal action, in particular a considerably more powerful ectoparasiticidal action, than isomer mixtures of 3-(2-chloro-2-(4-chloro-phenyl)-vinyl)-2,2-dimethyl-cyclopropane-1-carboxylic acid α-cyano-4-fluoro-3-phenoxybenzyl ester, which are known from the state of the art.

If, for example, (+)-trans-3-(Z-2-chloro-2-(4-chlorophenyl)-vinyl)-2,2-dimethyl-cyclopropane-1-carboxylic acid chloride and (S)-α-cyano-4-fluoro-3-phenoxy-benzyl alcohol or 4-fluoro-3-phenoxy-benzaldehyde and sodium cyanide are used as starting substances, the process according to the present invention is illustrated by the following equations:

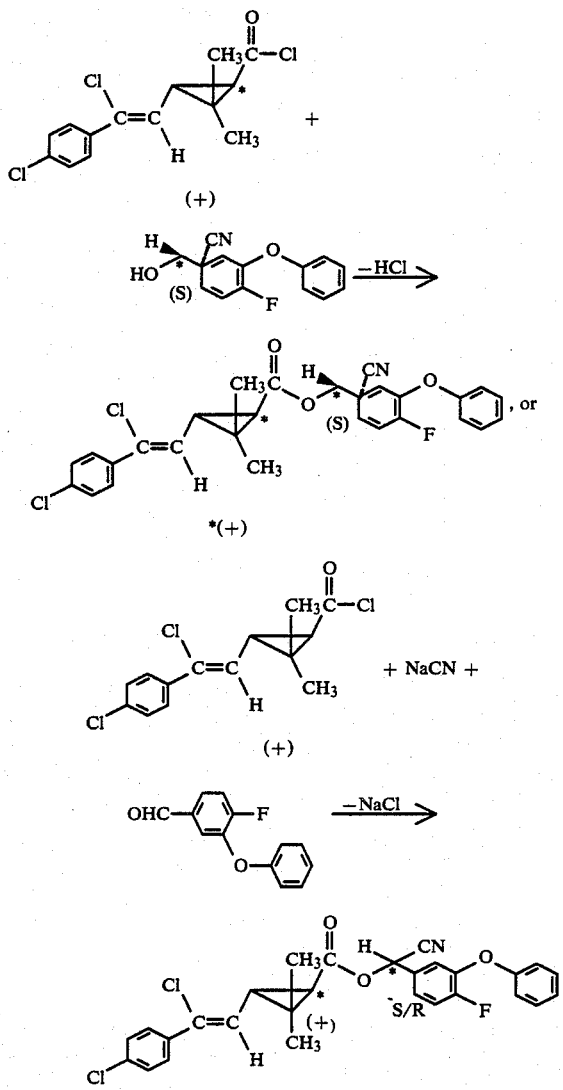

The diastereomer mixture of (+)-trans-Z-3-(2-chloro-2-(4-chlorophenyl)-vinyl)-2,2-dimethyl-cyclopropanecarboxylic acid (S)-α-cyano-3-phenoxy-4-fluorobenzyl ester and (+)-trans-Z-3-(2-chloro-2-(4-chlorophenyl)-vinyl)-2,2-dimethyl-cyclopropanecarboxylic acid (R)-α-cyano-3-phenoxy-4-fluorobenzyl ester which can be obtained by the latter process exemplified above can be resolved into the two individual components by known chromatographic methods, for example high pressure liquid chromatography, or by fractional crystallisation.

The optically active isomers of trans-3-(2-chloro-2-(4-chloro-phenyl)-vinyl-2,2-dimethyl-cyclopropane-1-carboxylic acid chloride of the formula (II) which are to be used as starting substances have not yet been described in the literature.

The present invention thus further relates to optically active isomers of trans-3-(2-chloro-2-(4-chlorophenyl)-vinyl)-2,2-dimethyl-cyclopropane-1-carboxylic acid, dextro-rotatory or laevo-rotatory isomers thereof, acid halides thereof and $C_1$ to $C_4$ alkyl esters thereof.

Examples of acid halides which may be mentioned are: (+)-trans-3-3(E/)-2-chloro-2-(4-chloro-phenyl)-vinyl)-2,2-dimethylcyclopropane-1-carboxylic acid chloride, (+)-trans-3-(E-2-chloro-2-(4-chloro-phenyl)-vinyl)-2,2-dimethylcyclopropane-1-carboxylic acid chloride and (+)-trans-3-(Z-2-chloro-2-(4-chlorophenyl)-vinyl)-2,2-dimethylcyclopropane-1-carboxylic acid chloride, and the corresponding laevo-rotatory compounds.

The new compounds of the formula (II) are obtained when a corresponding optically active isomer of trans-3-(2-chloro-2-(4-chloro-phenyl)-vinyl)-2,2-dimethylcyclopropane-1-carboxylic acid of the formula

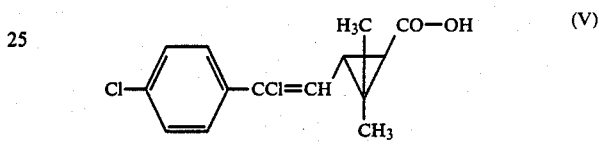

is reacted with a chlorinating agent (such as thionyl chloride), if appropriate in the presence of a diluent (such as carbon tetrachloride) at a temperature between 10° and 100° C.

Optically active isomers of trans-3-(2-chloro-2-(4-chloro-phenyl)-vinyl)-2,2-dimethyl-cyclopropane-1-carboxylic acid (V) have not yet been described in the literature.

The present invention thus further relates to (+)-trans-3-(E/Z-2-chloro-2-(4-chloro-phenyl)-vinyl-2,2-dimethyl-cyclopropane-1-carboxylic acid, (+)-trans-3-(E-2-chloro-2-(4-chloro-phenyl)-vinyl-2,2-dimethyl-cyclopropane-1-carboxylic acid and (+)-trans-3-(Z-2-chloro-2-(4-chlorophenyl)-vinyl)-2,2-dimethyl-cyclopropane-1-carboxylic acid, laevo-rotatory isomers thereof, acid halides thereof and $C_1$ to $C_4$ alkyl esters thereof.

Examples which may be mentioned are: (+)-trans-3-(E/Z-2-chloro-2-(4-chloro-phenyl)-vinyl)-2,2-dimethylcyclopropane-1-carboxylic acid, (+)-trans-3-(E-2-chloro-2-(4-chloro-phenyl)-vinyl)-2,2-dimethyl-cyclopropane-1-carboxylic acid and (+)-trans-3-(Z-2-chloro-2-(4-chlorophenyl)-vinyl)-2,2-dimethyl-cyclopropane-1-carboxylic acid, and the corresponding laevo-rotatory isomers.

The optically active isomers of trans-3-(2-chloro-2-(4-chloro-phenyl)-vinyl)-2,2-dimethyl-cyclopropane-1-carboxylic acid can be obtained from racemic mixtures of (V) by customary methods of concentration or resolution (see DE-OS (German Published Specification) No. 2,826,952, corresponding to U.S. Ser. No. 43,981 filed Feb. 28, 1979). These resolution or concentration operations are in general carried out by fractional precipitation or crystallisation of the salts with optically active amines or of the esters with optically active alcohols, in the particular optically active diastereomers; a particular process is described below.

An earlier, as yet unpublished, Patent Application corresponding to German Patent Application No. P 2,936,864, corresponding to U.S. Ser. No. 182,356 filed Aug. 29, 1980, relates to the preparation of racemic mixtures of the diastereomeric forms of trans-3-(2-chloro-2-(4-chlorophenyl)-vinyl)-2,2-dimethyl-cyclopropane-1-carboxylic acid.

(±)-Trans-3-(E/Z-2-chloro-2-(4-chloro-phenyl)-vinyl)-2,2-dimethyl-cyclopropane-1-carboxylic acid of the formula (V) is obtained by saponification of a corresponding alkyl ester of the formula

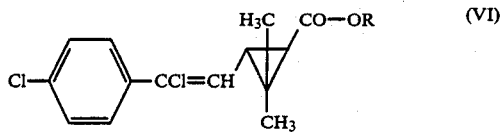

in which

R₂ represents a $C_1$ to $C_4$ alkyl radical, by customary methods, for example by heating the ester to a temperature between 50° and 100° C. with an alkali metal hydroxide solution (such as aqueous-alcoholic sodium hydroxide solution). For working up, the alcohol is distilled off, if appropriate, and the product is extracted with a water-immiscible solvent (such as methylene chloride) and the extracting agent is distilled off under reduced pressure.

Examples of the esters of the formula (VI) which may be mentioned are: (±)-trans-3-(E/Z-2-chloro-2-(4-chlorophenyl)-vinyl)-cyclopropane-1-carboxylic acid methyl ester, ethyl ester, n-propyl ester, iso-propyl ester, n-butyl ester, iso-butyl ester, sec.-butyl ester and tert.-butyl ester.

The esters of the formula (VI) have not yet been described in the literature. They are obtained by reacting a (±) trans-3-formyl-2,2-dimethyl-cyclopropane-1-carboxylic acid ester of the formula

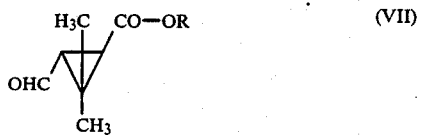

in which

R represents a $C_1$ to $C_4$ alkyl radical, with a 4-chloro-α-chloro-benzyl-phosphonic acid ester of the formula

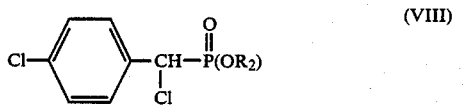

in which

R₂ represents a $C_1$ to $C_4$ alkyl radical, in the presence of a base (such as sodium methylate) and, if appropriate, in the presence of a diluent (such as ethanol and/or tetrahydrofuran) at a temperature between −10° and +50° C. For working up, the mixture is diluted with water and extracted with a water-immiscible solvent (such as methylene chloride). The extracts are dried and filtered and the solvent is distilled off under reduced pressure.

Esters of the formula (VII) are already known (see DE-OS (German Published Specification No. 2,615,160). Examples which may be mentioned are:

(±)-trans-3-formyl-2,2-dimethyl-cyclopropane-1-carboxylic acid methyl ester, ethyl ester, n-propyl ester, iso-propyl ester, n-butyl ester, iso-butyl ester, sec.-butyl ester and tert.-butyl ester.

4-Chloro-α-chloro-benzyl-phosphonic acid esters of the formula (VIII) are likewise already known (see DE-OS (German Published Specification) No. 2,827,101). Examples which may be mentioned are: 4-chloro-α-chlorobenzyl-phosphonic acid dimethyl ester and diethyl ester.

In addition to optically active isomers of trans-3-(2-chloro-2-(4-chloro-phenyl)-vinyl)-2,2-dimethylcyclopropane-1-carboxylic acid chloride (II), the individual enantiomers or the racemic mixture of α-cyano-4-fluoro-3-phenoxy-benzyl alcohol of the formula (III) or 4-fluoro-3-phenoxy-benzaldehyde of the formula (IV) are to be used as starting substances in the process according to the present invention.

4-Fluoro-3-phenoxy-benzaldehyde (IV) and racemic mixtures of α-cyano-4-fluoro-3-phenoxy-benzyl alcohol (III) are already known (see DE-OS (German Published Specification) No. 2,709,264).

The individual enantiomers of (III) can be separated by customary methods (see DE-OS (German Published Specification) No. 2,902,466).

Alkali metal cyanides which are to be used for the process according to the present invention are, preferably, sodium cyanide and potassium cyanide.

The process according to the present invention is preferably carried out using diluents. Possible diluents are virtually any of the inert organic solvents. These include, in particular, aliphatic and aromatic, optionally chlorinated hydrocarbons (such as pentane, hexane, heptane, cyclohexane, benzene, toluene, xylene, methylene chloride, chloroform, carbon tetrachloride, chlorobenzene and o-dichlorobenzene), ethers (such as diethyl ether and dibutyl ether, tetrahydrofuran, and dioxane), ketones (such as acetone, methyl ethyl ketone, methyl iso-propyl ketone and methyl isobutyl ketone) and nitriles (such as acetonitrile and propionitrile).

If 4-fluoro-3-phenoxy-benzaldehyde and sodium cyanide are used, water-immiscible solvents from the abovementioned group are preferably used, in combination with water as a second solvent component, that is to say the process is carried out in a two-phase medium. Compounds which are usually employed as auxiliaries for the phase transfer of reactants in reactions in multiphase media can be used as catalysts. Tetraalkyl- and trialkyl-aralkyl-ammonium salts, such as, for example, tetrabutylammonium bromide, methyltrioctylammonium chloride and trimethylbenzylammonium bisulphate, may be mentioned in particular.

The reaction temperature is in general kept between 0° and 100° C., preferably between 10° and 50° C. The preparation process is usually carried out under normal pressure.

The starting substances are usually employed in equimolar amounts for carrying out the process according to the invention. An excess of one or other of the reactants provides no substantial advantages. The reaction is in general carried out in suitable diluents, if appropriate in the presence of a catalyst, and the reaction mixture is stirred at the required temperature for several hours. Thereafter, an organic solvent (such as toluene) is added and the organic phase is worked up in the customary manner, by washing, drying and distilling off the solvent.

The new compounds of the formula (I) are obtained in the form of oils and cannot be distilled without decomposition; however, they can be freed from the last volatile constituents by so-called "incipient distillation", that is to say by prolonged heating to moderately elevated temperatures under reduced pressure, and can be purified in this manner. They are characterised by the $(\alpha)_D$ value.

E/Z-Isomer mixtures of (±)-trans-3-(E/Z-2-chloro-2-(4-chloro-phenyl)-vinyl)-2,2-dimethyl-cyclopropane-1-carboxylic acid of the formula (V) (as defined above) can be separated by a procedure in which isomer mixtures of the acid of formula (V) are dissolved in a water-immiscible solvent (such as methylene chloride) and converted into the salt by adding 0.001 to 1, preferably 0.1 to 1, equivalent of a base (such as aqueous sodium hydroxide solution) in X steps, X representing a number between 1 and ∞, "∞" denoting a continuous procedure, but preferably representing 2 to 100, the salt is extracted with water, in X steps, after each addition of base, the individual aqueous fractions are acidified with a mineral acid (such as hydrochloric acid) and extracted with a water-immiscible solvent (such as methylene chloride), each individual extract is worked up by customary methods, for example by drying, filtering, and distilling off the solvent, and the fractions in which, according to analysis by NMR spectroscopy, one of the isomers (Z or E) predominates are recrystallised from an organic solvent, preferably a hydrocarbon with 5 to 10 carbon atoms.

A further method for separating E/Z-acid mixtures consists of a procedure in which isomer mixtures of the acid (V) are dissolved in an aqueous alkali metal hydroxide solution (such as sodium hydroxide solution) which contains exactly one base equivalent, the acid is produced again by adding 0.001 to 1, preferably 0.1 to 1, equivalent of a mineral acid in X steps, X representing a number between 1 and ∞, "∞" denoting a continuous procedure, but preferably between 2 and 100, the acid is extracted, after each addition of acid, with a water-immiscible organic solvent (such as methylene chloride), each individual extract is worked up by customary methods, for example by drying, filtering, and distilling off the solvent, and the fractions in which, according to analysis by NMR spectroscopy, one of the isomers (Z or E) predominates are recrystallised from an organic solvent, preferably a hydrocarbon with 5 to 10 carbon atoms. As already mentioned, (±)-diastereomer mixtures of E/Z-, E- or Z-trans-3-(2-chloro-2-(4-chloro-phenyl)-vinyl)-2,2-dimethylcyclopropane-1-carboxylic acid of the formula (V) (as defined above) can be resolved by customary methods (see DE-OS (German Published Specification) No. 2,826,952).

Such mixtures can be resolved, for example, by a procedure in which the mixtures or corresponding alkali metal salts are heated to temperatures between 50° and 100° C. with D-(−)-threo-2-amino-1-(4-nitrophenyl)-1,3-propanediol or its hydrochloride in water-/alcohol mixtures until solution is virtually complete, and the solutions are allowed to cool slowly to temperatures between 0° and 30° C. Salts in which the (+)-isomers are concentrated crystallise out, whilst the salts of the (−)-isomers predominantly remain in solution. After separation by filtration—the (+)-isomer can then be concentrated still further by recrystallisation—the corresponding acids can be liberated, by acidification with strong acids, from the salts which are present in the crystals or in the mother liquor and in which the individual diastereomers are concentrated. For example, the crystals, which predominantly contain the salt of (±)-trans-Z-3-(2-chloro-2-(4-chloro-phenyl)-vinyl)-2,2-dimethyl-cyclopropane-1-carboxylic acid and D-(−)-threo-2-amino-1-(4-nitro-phenyl)-1,3-propanediol are dispersed in a two-phase system of methylene chloride and dilute hydrochloric acid and the mixture is stirred intensively for some minutes. The organic phase is then separated off, dried and filtered. The solvent is carefully distilled off from the filtrate under reduced pressure, (+)-trans-Z-3-(2-chloro-2-(4-chlorophenyl)-vinyl)-2,2-dimethyl-cyclopropane-1-carboxylic acid being obtained as the residue.

The active compounds according to the invention are suitable for combating ectoparasites in the field of veterinary medicine.

The present invention thus also provides an ectoparasiticidal composition containing as active ingredient a compound of the present invention in admixture with an inert and veterinary carrier, i.e., a solid or liquefied gaseous diluent or carrier or in surface-active agent.

The present invention also provides a method of combating ectoparasites which comprises applying to the ectoparasites, or to a habitat thereof, a compound of the present invention alone or in the form of a composition containing as active ingredient a compound of the present invention in admixture with a diluent or carrier.

The present invention also provides a method of freeing or protecting domesticated animals from ectoparasites which comprises applying to said animals a compound according to the present invention, in admixture with a diluent or carrier.

The present invention further provides domesticated animals whenever freed or protected from ectoparasites by the application to said animals of a compound according to the present invention, in admixture with a diluent or carrier.

The active compounds according to the invention are used in a known manner in the veterinary sector, such as by oral administration, for example in the form of tablets, capsules, drinks and granules, by dermal application, for example in the form of dipping, spraying, pouring on and spotting on, and dusting, and by parenteral administration, for example in the form of an injection.

PREPARATIVE EXAMPLES

Example 1

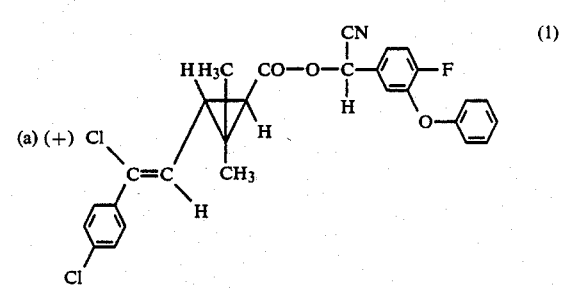

3.4 g (0.0112 mole) of (+)-trans-Z-3-(2-chloro-2-(4-chloro-phenyl)-vinyl)-2,2-dimethyl-1-cyclopropanecarboxylic acid chloride, dissolved in 10 ml of cyclohexane, were added dropwise to a mixture of 50 ml of cyclohexane, 0.87 g of sodium cyanide, 1.3 ml of water, 2.42 g (0.0112 mole) of 3-phenoxy-4-fluorobenzaldehyde and 0.2 g of tetrabutylammonium bromide at 20°–25° C., whilst stirring, and the mixture was then stirred at 20°–25° C. for 4 hours. 100 ml of toluene were then added to the reaction mixture and the mixture was extracted twice by shaking with 60 ml of water each time. The organic phase was separated off and dried over magnesium sulphate and the solvent was distilled off under a waterpump vacuum. Last residues of solvent were removed by brief incipient distillation at a bath temperature of 60° C./1 mm Hg. 4.4 g (77% of theory) of (+)-trans-Z-3-(2-chloro-2-(4-chloro-phenyl)vinyl)-2,2-dimethyl-cyclopropane-carboxylic acid (±)-α-cyano-3-phenoxy-4-fluoro-benzyl ester were obtained as a viscous oil with an optical rotation $[\alpha]_D$ of +58.2° (C=100 mg in 10 ml of CHCl$_3$).

$^1$H-NMR spectrum in CDCl$_3$/TMS τ(ppm).
Benzyl-H: 3.60 (S/$^1$/2H) and 3.64 (S/$^1$/2H).
Vinyl-H: 4.12 (d/1H).

Separation of the α-R and α-S diastereomers:

5 gg of (+)-trans-Z-3-(2-chloro-2-(4-chloro-phenyl)-vinyl)-2,2-dimethyl-cyclopropane-carboxylic-acid-(RS)-α-cyano-3-phenoxy-4-fluoro-benzylester were subjected to preparative high pressure liquid chromatography.

Column: 250 mm×21,2 mm, 7μ silica gel.
Mobile phase: 47,6% Vol. of n-hexane, 47,6% Vol. of cyclohexane and 4,8% Vol. of diethyl ether.
Amount flowing through: 30 ml/minute
Amount applied: 30 mg

| Retention volume: | Fraction I: 300 ml |
|---|---|
|  | Fraction II: 330 ml |

The two fractions were then freed from solvent in vacuo. As Fraction I, 0,9 g of (+)-trans-Z-3-(2-chloro-2-(4-chloro-phenyl)-vinyl)-2,2-dimethyl-cyclopropane-carboxylic-acid-(R)-α-cyano-3-phenoxy-4-fluoro-benzylester were obtained as a colourless oil.

$[\alpha]_D^{20}$ = +41,0° C. (c=190 mg in 10 ml CHCl$_3$).

$^1$H-NMR-spectrum (CDCl$_3$/TMS) cppm): —CHCN: 6,351 (S/1H), dimethyl-H: 1,37 (S/3H) and 1,26 (S/3H).

As Fraction II, 0,5 g of (+)-trans-Z-3-(2-chloro-2-(4-chloro-phenyl)-vinyl)-2,2-dimethyl-cyclopropane-carboxylic-acid-(S)-αcyano-3-phenoxy-4-fluoro-benzylester were obtained as a colourless oil.

$[d]_D^{20}$ = +34,5° C. (c=120 mg in 10 ml CHCl$_3$).

$^1$H-NMR-spectrum (CDCl$_3$/TMS) cppm): —CHCN: 6,377 (S/1H), dimethyl-H: 1,28 (S/3H) and 1,22 (S/3H).

(b) The preparation of the starting compounds:

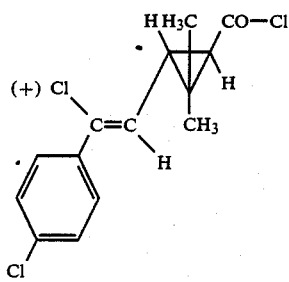

4.2 g (0.0147 mole) of (+)-trans-Z-3-(2-chloro-2-(4-chloro-phenyl)-vinyl)-2,2-dimethyl-1-cyclopropane-carboxylic acid were dissolved in 50 ml of carbon tetrachloride, and 8.8 g of thionyl chloride were slowly added dropwise at 40° C., whilst stirring. The mixture was then heated under reflux for 4 hours. At the end of the reaction time, excess thionyl chloride and carbon tetrachloride were distilled off under a waterpump vacuum. Last residues of solvent were removed by brief incipient distillation at a bath temperature of 60° C./2 mm Hg. 4.0 g (89.7% of theory) of (+)-trans-Z-(3-(2-chloro-2-(4-chloro-phenyl)-vinyl)-2,2-dimethyl-cyclopropane-carboxylic acid chloride were obtained as a crystalline solid with a melting point of 65°–70° C.

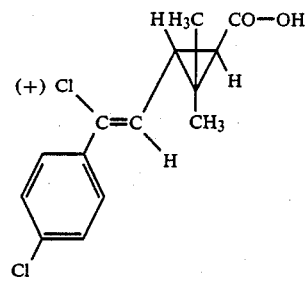

A mixture of 25 ml of concentrated hydrochloric acid in 100 ml of water was added to 8.8 g (0.0177 mole) of the salt of (+)-trans-Z-3-(2-chloro-2-(4-chlorophenyl)-vinyl)-2,2-dimethyl-1-cyclopropanecarboxylic acid and D-(—)-threo-2-amino-1-(4-nitro-phenyl)-1,3-propanediol, suspended in 100 ml of methylene chloride, and the mixture was then stirred intensively. The organic phase was then separated off and dried over magnesium sulphate and the solvent was distilled off under a water-pump vacuum. Last residues of solvent were removed by brief incipient distillation at a bath temperature of 60° C./1 mm Hg. 4.5 g (89.2% of theory) of (+)-trans-Z-3-(2-chloro-2-(4-chloro-phenyl)-vinyl)-2,2-dimethyl-1-cyclopropane-carboxylic acid were obtained as colourless crystals with a melting point of 105°–106° C. and an optical rotation, $[\alpha]_D$ of +122° (C=100 mg in 10 ml of CHCl$_3$).

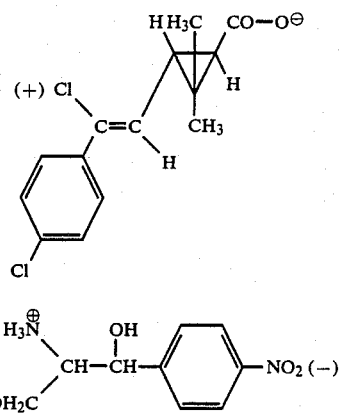

(A) A mixture of 2.85 g (0.01 mole) of (±)-trans-Z-3-(2-chloro-2-(4-chloro-phenyl)-vinyl)-2,2-dimethyl-1-cyclopropanecarboxylic acid and 2.12 g (0.01 mole) of D-(—)-threo-2-amino-1-(4-nitro-phenyl)-1,3-propanediol in 180 ml of a mixture of 7 parts by volume of water and 3 parts by volume of ethanol was heated to 65°–70° C., whilst stirring, until a clear solution was obtained. The solution was then allowed to cool slowly to room temperature (20° C.) and was subsequently left to stand at 20° C. for a further 6 hours. The crystals which had precipitated were filtered off and recrystallised agains from the water/ethanol mixture 7:3. 0.92 g (37% of theory) of the salt of (+)-trans-Z-3-(2-chloro-2-(4-chloro-phenyl)-vinyl)-2,2-dimethyl-cyclopropane-1-carboxylic acid and D-(—)-threo-2-amino-1-(4-nitro-phenyl)-1,3-propanediol was obtained as colourless, nacreous flakes with a melting point of 160°-162° C.

(B) A mixture of 28.5 g (0.1 mole) of (±)-trans-Z-(3-(2-chloro-2-(4-chloro-phenyl)-vinyl)-2,2-dimethyl-cyclopropane-1-carboxylic acid, 540 ml of ethanol, 1260 ml of water and 4 g (0.1 mole) of sodium hydroxide was warmed to 70°-75° C., whilst stirring, until a clear solution had formed. 12.5 g (0.05 mole) of D-(—)-threo-2-amino-1-(4-nitro-phenyl)-1,3-propanediol hydrochloride, dissolved in 80 ml of water, was added to this mixture, whilst stirring, and the mixture was warmed again to 70°-75° C. for 10 minutes. It was then allowed to cool slowly to room temperature, without stirring, and was subsequently left to stand for a further 5 hours at 20° C. The crystals which had precipitated were filtered off and recrystallised again from a water/ethanol mixture 7:3. 8.8 g (35.4% of theory) of the amine salt of (+)-trans-Z-(3-(2-chloro-2-(4-chloro-phenyl)-vinyl)-2,2-dimethyl-cyclopropane-1-carboxylic acid and D-(—)-threo-2-amino-1-(4-nitro-phenyl)-1,3-propanediol were obtained as colourless crystals with a melting point of 157°-160° C.

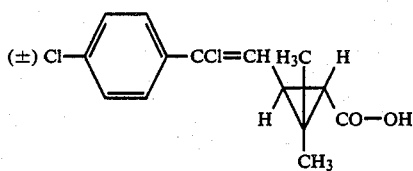

22.2 g (0.071 mole) of (±)-trans-3-(E/Z-2-chloro-2-(4-chloro-phenyl)-vinyl)-2,2-dimethyl-cyclopropane-carboxylic acid ethyl ester were dissolved in 100 ml of ethanol, a solution of 5.7 g of sodium hydroxide in 100 ml of water was added and the mixture was heated under reflux for 4 hours, whilst stirring. The ethanol was then distilled off under a waterpump vacuum, the residue was taken up in 300 ml of warm water and the mixture was extracted once with 300 ml of methylene chloride. The aqueous phase was separated off, acidified with concentrated hydrochloric acid and then extracted twice with 300 ml of methylene chloride. The organic phase was separated off over magnesium sulphate and dried and the solvent was distilled off under a waterpump vacuum. Last residues of solvent were removed by brief incipient distillation at a bath temperature of 60° C./2 mm Hg. 15.5 g (76.6% of theory) of (±)-trans-3-(E/Z-2-chloro-2-(4-chloro-phenyl)-vinyl)-2,2-dimethyl-cyclopropane-carboxylic acid were obtained as a viscous oil which crystallises after some time. After recrystallisation from acetonitrile, the product had a melting point of 120°-132° C.

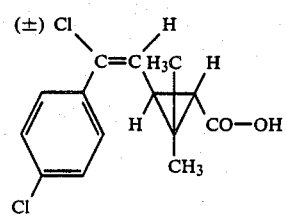

31.6 g (0.111 mole) of (±)-trans-(E/Z-2-chloro-2-(4-chloro-phenyl)-vinyl)-2,2-dimethyl-cyclopropane-car- boxylic acid with an E/Z ratio of 60:40 were dissolved in 50 ml of methylene chloride and the solution was extracted by shaking with a solution of 0.885 g (0.022 mole) of sodium hydroxide in 50 ml of water. The aqueous phase was then separated off. This operation was then repeated 4 more times. 5 fractions of an aqueous hydrochloric acid solution were thus obtained, and were then each by themselves acidified with concentrated hydrochloric acid and subsequently extracted with in each case 2 50 ml portions of methylene chloride. The organic phases were separated off and dried over magnesium sulphate and the solvent was then stripped off in vacuo. 5 fractions of the above acid with a different E/Z ratio were thus obtained. The E/Z ratio was determined from the $^1$H-NMR spectrum.

Fraction I: that is to say the acid separated off first, had an E/Z ratio of 50/50.

Fraction V: has an E/Z ratio of 87/13.

Fraction V (5 g) was then dissolved in cyclohexane at 30°-40° C. On leaving the solution to stand at room temperature, (±)-trans-3-(E-2-chloro-2-(4-chloro-phenyl)-vinyl)-2,2-dimethyl-cyclopropane-carboxylic acid crystallised out in the form of colourless crystals of melting point 138°-139° C. The structure was confirmed by the $^1$H-NMR spectrum.

$^1$H-NMR spectrum in CDCl$_3$/TMS, τ(ppm): aromatic-H: 2.43-2.74 (M/4H), vinyl-H: 4.24 (d/1H), cyclopropane-H: 7.74-8.04 (m/1H) and 8.39 (d/1H), and dimethyl-H: 8.73 (s/6H).

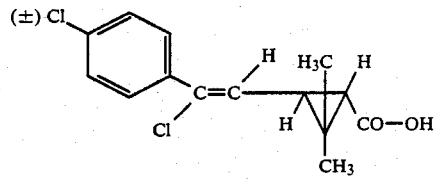

130.2 g (0.4568 mole) of (±)-trans-(E/Z-2-chloro-2-(4-chloro-phenyl)-vinyl)-2,2-dimethyl-cyclopropane-carboxylic acid with an E/Z ratio of 60/40 were suspended in 500 ml of water and were converted into the sodium salt by adding 18.27 g (0.4568 mole) of sodium hydroxide, dissolved in 100 ml of water, whilst stirring. Under the aqeuous salt solution was introduced a layer of 100 ml of methylene chloride, and 0.04568 mole of hydrogen chloride was added in the form of a 37% strength aqueous solution, whilst stirring vigorously. The mixture was then stirred for a further 5 minutes and the methylene chloride phase was subsequently separated off. The acidification and separation was repeated in the same manner a further 9 times in total. The 10 methylene chloride phases were then dried over magnesium sulphate and the solvent was subsequently stripped off in vacuo. 10 fractions of the above acid with a different E/Z ratio were thus obtained. The E/Z ratio was determined from the $^1$H-NMR spectrum.

Fraction I: (acid separated off first) had an E/Z ratio of 85/15.

Fraction IX: had an E/Z ratio of 40/60.

Fraction IX (10.4 g) was then dissolved in cyclohexane at 30°-40° C. On leaving the solution to stand at room temperature, (±)-trans-3-(Z-2-chloro-2-(4-chlorophenyl)-vinyl)-2,2-dimethyl-cyclopropane-carboxylic acid separated out in the form of colourless crystals of melting point 141°-142° C. The structure was confirmed by the $^1$H-NMR spectrum.

¹H-NMR spectrum in CDCl₃/TMS (ppm): aromatic-H: 2.37–2.81 (M/4H), vinyl-H: 4.10 (d/1H), cyclopropane-H: 7.26–7.56 (m/1H) and 8.26 (d/1H) and dimethyl-H: 8.55 (s/3H) and 8.70 (s/3H).

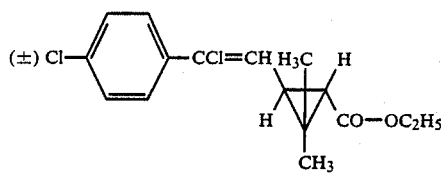

2.53 g (0.11 mole) of sodium were dissolved in portions in 50 ml of ethanol. When all the sodium had dissolved, 150 ml of tetrahydrofuran (anhydrous) were added, and 29.7 g (0.1 mole) of 4-chloro-α-chloro-benzylphosphonic acid diethyl ester, dissolved in 30 ml of anhydrous tetrahydrofuran, were added dropwise at 0° C., whilst stirring. After the mixture had subsequently been stirred for a further 2 hours at 0°–5° C., 17 g (0.1 mole) of trans-2,2-dimethyl-3-formyl-cyclopropanecarboxylic acid ethyl ester, dissolved in 30 ml of anhydrous tetrahydrofuran, were added dropwise at 0° C., whilst stirring. Stirring was continued for a further 12 hours at 20°–25° C. 500 ml of water were then added to the reaction mixture and the mixture was extracted twice with 300 ml of methylene chloride each time. The organic phase was separated off and dried over magnesium sulphate, the solvent was distilled off under a waterpump vacuum and the residue was distilled in vacuo. 23.2 g (74.1% of theory) of (±)-trans-3-(E/Z-2-chloro-2-(4-chloro-phenyl)-vinyl)-2,2-dimethyl-cyclopropanecarboxylic acid ethyl ester were obtained as a yellow oil with a boiling point of 155°–165° C./1 mm Hg.

The pesticidal activity of the compounds of this invention is illustrated by the following biotest-Example.

In this Example, the compound according to the present invention is identified by the number (given in brackets) of the corresponding preparative Example.

EXAMPLE

Test with Boophilus microplus resistant

| Solvent: | 35 parts by weight of ethylene glycol monomethyl ether |
| --- | --- |
| | 35 parts by weight of nonylphenol polyglycol ether |

To produce a suitable preparation of active compound, three parts by weight of the solvent mixture indicated above, and the concentrate thus obtained was diluted with water to the desired concentration.

10 adult Boophilus microplus res. were immersed for 1 minute in the active compound preparation to be tested. After transfer to plastic beakers and storage in a climatically controlled chamber, the degree of destruction was determined.

In this test, for example, the compound (1) showed a superior activity compared to the prior art.

The test results are given in the following table:

TABLE I

| Active compound | Concentration in ppm | Destruction in % Boophilus microplus (OP-res. Biarra-St.) |
| --- | --- | --- |
| Fraction I of the compound obtained according to example 1 | 10 | 100 |
| | 3 | 100 |
| | 1 | >50 |
| | 0,3 | <50 |
| | 0,1 | 0 |
| | 0,03 | 0 |
| | 0,01 | 0 |
| Fraction II of the compound obtained according to example 1 | 10 | 100 |
| | 3 | 100 |
| | 1 | 100 |
| | 0,3 | >50 |
| | 0,1 | >50 |
| | 0,03 | <50 |
| | 0,01 | 0 |

What is claimed is:

1. An optically active isomer of trans-3-(2-chloro-2-(4-chloro-phenyl)-vinyl)-2,2-dimethylcyclopropane-1-carboxylic acid a-cyano-4-fluoro-3-phenoxybenzyl ester of the formula

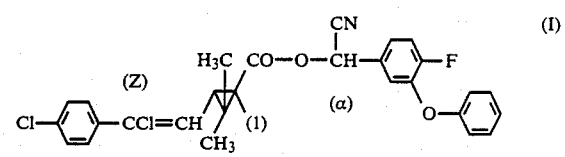

in which the configuration is
(a) 1R, trans Z, α-S (b) 1R, trans Z, αR/S.

2. A method of combating ectoparasites, which comprises applying to the ectoparasites, or to a habitat thereof, an ectoparasiticidally effective amount of a compound according to claim 1 alone or in the form of a composition containing as active ingredient an ectoparasitically effective amount of a compound according to claim 1 in admixture with an inert diluent or carrier.

3. Compounds according to claim 1, in which the symbols "Z", (+) and (−) and "R" and "S" mean that the compounds are enriched in the isomers of the particular configuration given to the extent of more than 90% by weight.

4. A method of freeing or protecting domesticated animals from ectoparasites, which comprises applying an ectoparasiticidally effective amount of a compound according to claim 1 in admixture with a diluent or carrier.

5. An ectoparasiticidal composition, characterised in that it comprises as active ingredient a compound according to claim 1 in admixture with an inert veterinary carrier.

* * * * *

UNITED STATES PATENT AND TRADEMARK OFFICE
CERTIFICATE OF CORRECTION

PATENT NO. : 4,772,629
DATED : Sep. 20, 1988
INVENTOR(S) : Fuchs et al.

It is certified that error appears in the above-identified patent and that said Letters Patent is hereby corrected as shown below:

Col. 8, Line 3    Delete "(±)" and substitute --(+)--
Col. 9, Line 19   Delete "gg" and substitute --g--

Signed and Sealed this

Thirteenth Day of June, 1989

Attest:

DONALD J. QUIGG

*Attesting Officer*   *Commissioner of Patents and Trademarks*